United States Patent
Taday et al.

(10) Patent No.: US 7,675,036 B2
(45) Date of Patent: Mar. 9, 2010

(54) REDUCING SCATTERING RELATED FEATURES IN TERHERTZ TIME DOMAIN SPECTROSCOPY BY AVERAGING THE IMPULSE WAVEFORM OVER A PLURALITY OF SAMPLE POINTS

(75) Inventors: Philip F. Taday, Cambridge (GB); Yao-Chun Shen, Cambridge (GB)

(73) Assignee: Teraview Limited, Cambridge (GB)

( * ) Notice: Subject to any disclaimer, the term of this patent is extended or adjusted under 35 U.S.C. 154(b) by 0 days.

(21) Appl. No.: 11/661,090

(22) PCT Filed: Aug. 26, 2005

(86) PCT No.: PCT/GB2005/003333

§ 371 (c)(1),
(2), (4) Date: Mar. 27, 2007

(87) PCT Pub. No.: WO2006/021799

PCT Pub. Date: Mar. 2, 2006

(65) Prior Publication Data

US 2008/0006767 A1    Jan. 10, 2008

(30) Foreign Application Priority Data

Aug. 26, 2004  (GB) ................................. 0419098.9

(51) Int. Cl.
*G01J 5/02* (2006.01)
(52) U.S. Cl. .................................................. 250/341.1
(58) Field of Classification Search ............... 250/341.1
See application file for complete search history.

(56) References Cited

U.S. PATENT DOCUMENTS 5,710,430 A    1/1998  Nuss 6,777,684 B1    8/2004  Volkov et al.

FOREIGN PATENT DOCUMENTS

| EP | 0 864 857 A1 | 9/1998 |
| EP | 1 469 298 | 10/2004 |
| GB | 2 380 920 | 4/2003 |
| GB | 2 397 207 A | 7/2004 |

(Continued)

OTHER PUBLICATIONS

Mittleman, D. et al., "Recent Advances in Terahertz Imaging", Applied Physics B: Lasers and Optics, Springer Interntational, Berlin, DE, vol. B68, No. 6, Jun. 1999, pp. 1085-1094.

(Continued)

*Primary Examiner*—David P Porta
*Assistant Examiner*—Marcus H Taningco
(74) *Attorney, Agent, or Firm*—Dickstein Shapiro LLP

(57) ABSTRACT

A method of investigating an object, comprising the steps of: (a) irradiating the object with an optically-generated pulse of electromagnetic radiation, said pulse having a plurality of frequencies in the range from 100 GHz to 100 THz; (b) detecting radiation transmitted and/or reflected from the object to obtain a time domain waveform; (c) repeating steps (a) and (b) for a plurality of points on the object and (d) combining data from step (c) to produce a time domain waveform for the object which has been averaged over the plurality of points.

3 Claims, 13 Drawing Sheets

FOREIGN PATENT DOCUMENTS

| | | |
|---|---|---|
| WO | WO 02/17231 | 2/2002 |
| WO | WO 03/058212 | 7/2003 |
| WO | WO 2005/019807 | 3/2005 |
| WO | WO 2005/119214 A1 | 12/2005 |
| WO | WO 2006/008456 A1 | 1/2006 |

OTHER PUBLICATIONS

Cheville, R. et al., "Time Resolved Measurements Which Isolate the Mechanisms Responsible for Terahertz Glory Scattering from Dielectric Spheres", Physical Review Letters APS USA, vol. 80, No. 2. Jan. 12, 1998, pp. 269-272.

Grischkowsky, D., "Optoelectronic THz Impulse Ranging", Oct. 6, 2000, http://stinet.dtic.mil/cgi-bin/GetTRDoc?AD=ADA384379&Location=U2&doc=GetTRDoc.pdf>.

Loffler, T. et al., "Terahertz Dark-Field Imaging of Biomedical Tissue", Optics Express, Optical Society of America, Washington, DC, US, vol. 9, No. 12, Dec. 3, 2001, pp. 616-621.

Loffler, T. et al., "Visualization and Classification in Biomedical Terahertz Pulsed Imaging", Physics in Medicine and Biology, Taylor and Francis LTD., London, GB, vol. 47, No. 21, Nov. 7, 2002, pp. 3847-3852.

Hu, B. et al., "Imaging with Terahertz Waves", Optics Letters, OSA, Optical Society of America, Washington, DC, US, vol. 20, No. 16, Aug. 15, 1995, pp. 1716-1718, 1718A.

Hunsche, S. et al., "New Dimensions in T-Ray Imaging", IEICE Transactions on Electronics, Electronics Society, Tokyo, JP, vol. E81-C, No. 2, Feb. 1998, pp. 269-275.

Pickwell et al., "In Vivo Study of Human Skin Using Pulsed Terahertz Radiation" Physics in Medicine and Biology IOP, vol. 49, No. 9, pp. 1595-1607, May 7, 2004.

Weide Van Der et al., "Spectroscopy with Electronic Terahertz Techniques" Proceedings of the SPIE, vol. 3828, pp. 276-284, Jun. 1999.

Shen Yaochun et al., : Terahertz Spectroscopy of Explosive Materials Proceedings of SPIE The International Society for Optical Engineering; Passive Millimetre-wave and Terahertz Imaging and Technology, vol. 5619, pp. 82-89, 2004.

Tribe et al., "Hidden Object Detection: Security Applications of Terahertz Technology" Proceedings of the SPIE, vol. 5354, pp. 168-176, Apr. 2004.

Shen et al.,"Determination of Glucose Concentration in Whole Blood Using Fourier-Transform Infrared Spectroscopy" Journal of Biological Physics, vol. 29, No. 2-3, pp. 129-133.

REDUCING SCATTERING RELATED FEATURES IN TERHERTZ TIME DOMAIN SPECTROSCOPY BY AVERAGING THE IMPULSE WAVEFORM OVER A PLURALITY OF SAMPLE POINTS

The present invention relates generally to the field of apparatus and methods for imaging and/or investigating samples in the far-infrared (far-IR)/Terahertz (THz) frequency range from 100 GHz to 100 THz. Preferably the radiation utilised is in the frequency range of 500 GHz to 100 THz and more preferably from 1 THz to 100 THz and most preferably from 700 GHz to 10 THz.

It is well established that many chemicals and pharmaceutical agents have spectral signatures in the THz region. The reason for the spectral signals in this frequency range is considered to be associated with inter-molecular or intra-molecular crystalline vibrations or collective phonon oscillations. It is known that in THz spectroscopy the spectral information of transmitted and/or scattered radiation can be used to identify materials. Most materials interact with terahertz waves to some degree, and each material has its own frequency pattern, which can be considered as a kind of 'fingerprint'.

Of late security concerns have increased the need for a system that is able to identify hidden explosives, such as under a person's clothing, in a person's suitcase or in a postal package.

US Patent Application Number 2001/0033636 discloses a method of detecting explosives in luggage which uses X-rays to determine an average atomic number of a material. The average atomic number is then compared with known average atomic numbers of explosive materials to determine if the material being examined is an explosive. This technique, however is unsuitable for routine-security screening of people as its radiation is ionising.

In a paper entitled "Spectroscopy with electronic terahertz techniques" by D. W. van der Weide et al published in Proc Spie 3828 (99), electronic pulses in the microwave range, up to 450 GHz, are used to investigate explosives. These pulses are generated electronically using non-linear transmission lines, coupled with varactor diodes that are patterned on a semiconductor. A sine wave is applied to the transmission line and the result at the other end is a rapid (1-2 ps) voltage step, which is used to produce the microwave pulse from the semiconductor device. This paper demonstrates spectral features of explosives, but only in the sub-terahertz or microwave frequency range.

THz radiation is suitable for screening people and their possessions as it is non-ionising and can pass through clothing, paper, cardboard, wood, masonry, plastic and ceramics. Therefore, it is safer than x-ray techniques.

It has been speculated that THz radiation could be used to obtain spectral information of explosive materials, as the organic molecular nature of explosives, and their crystalline structure are of the appropriate form. To date, however, this has not been effectively achieved.

Many practical embodiments of THz systems utilise the transmission of THz radiation through the sample under investigation to a detector. In laboratory conditions samples can be prepared to avoid attenuation effects. However, in practice, samples are often granulated which leads to scattering of the irradiating radiation. Terahertz pulse spectroscopy is a coherent detection system which means that it has a large dynamic range. However, the effects of scattering or attenuation means that a THz signal may be too weak to detect in certain samples.

THz systems which utilise the reflection of THz radiation from a sample will not be limited by attenuation effects in the same way that transmission-based systems are. However, reflection-based systems experience different problems which in practice has meant that effective THz reflection spectroscopy is not possible.

In any THz system emitted Thz radiation will impinge upon the surface of the object under investigation. The surface of the object represents an interface between a medium with a first refractive index (usually air) and the object itself (which has a second refractive index which is different to the first refractive index).

The difference in the refractive indices means that a proportion of the radiation will be transmitted into the object (for an air/polythene interface this amounts to around 96% of the incident radiation) and a proportion will be reflected (for the air/PE example this therefore equates to around 4% of the incident radiation).

It can therefore be seen that the reflected beam will always have a weaker intensity than the transmitted beam. This means that the reflected beam is more susceptible to noise such as scattered radiation.

A further problem arises when the sample under investigation comprises scattering centres capable of scattering any radiation that penetrates the object. For both transmission based and reflection based systems the arrival times of radiation arriving at the detector from the surface of the object and scattering centres will be different. For reflection the time of arrival will depend on the depth of the scattering centre from the surface of the object. For transmission based systems the time of arrival depends on the extra path length the scattered radiation has travelled relative to radiation that has directly passed through the object. This spread of arrival times causes artificial spectral features which can either mask actual features or create false features.

One technique for mitigating the effects of scattering is to window the radiation detected at the detecting means. By gating the arrival time within which the system will detect photons any late arriving photons (from scattering events) will not be detected. Such a technique however reduces the efficiency of any spectroscopic analysis of the sample in question as it inevitably loses spectral information.

It is therefore an aim of the present invention to overcome or alleviate at least some of the problems associated with both transmission based and reflection based prior art systems.

According to first aspect the present invention provides a method of investigating an object, comprising the steps of:
(a) irradiating the object with an optically-generated pulse of electromagnetic radiation, said pulse having a plurality of frequencies in the range from 100 GHz to 100 THz;
(b) detecting radiation transmitted and/or reflected from the object to obtain a time domain waveform;
(c) repeating steps (a) and (b) for a plurality of points on the object and
(d) combining data from step (c) to produce a time domain waveform for the object which has been averaged over the plurality of points.

The invention which is the subject of the present invention is suitable for use in both transmission based systems and also reflection based systems. The method comprises irradiating the object under investigation and detecting the radiation reflected/transmitted from a point on the object. The irradiation/detection steps are then repeated for a plurality of points such that an averaged time domain waveform can be calculated for the object.

The method of the present invention acknowledges that signals due to scattering depend strongly on the geometry of the scattering centres within the object whereas directly reflected or transmitted signals do not. By taking repeated measurements the random signal elements introduced by scattering effects are removed and the true reflection/transmission signals, which have no phase dependence on the geometry of the object, remain.

In conventional optical spectroscopy methods, the intensity of the incident ($I_o(\nu)$) and the transmitted ($I_t(\nu)$) radiation is measured. The optical absorption coefficient, $\alpha(\nu)$, can then be calculated from the following equation:

$$T_{int}(\nu) \equiv I_t(\nu)/I_o(\nu) = e^{-2\alpha(\nu)d}$$

where $\nu$ is the frequency.

In terahertz pulsed spectroscopy (TPS) measurement however, the electric field, instead of the intensity, of the (THz) radiation is measured. The electric field of the transmitted THz radiation can be described as:

$$T(\nu) \equiv E_t(\nu)/E_o(\nu) = e^{-\alpha(\nu)d} e^{jk(\nu)d}$$

$$k(\nu) = n(\nu)2\pi\nu/c$$

The fact that the electric field is measured as opposed to the intensity of the radiation, as in other spectroscopic systems, allows the detected radiation to be "averaged" as claimed in this aspect of the invention. This is because the electric field, E, can be both positive and negative and so the scattering events will tend to cancel each other out over a large enough sampling of points whereas intensities will always add.

It is clear that both absorption coefficient ($\alpha(\nu)$) and refractive index ($n(\nu)$) can be calculated from a single measurement because the electric field measurements provide both amplitude and phase information.

At absorption peaks, the transmittance drops significantly from 100% to a few percent. Therefore the transmission measurement is very sensitive to absorption. The reflection loss at the air/sample interfaces, which is mainly determined by the refractive index difference, only causes a baseline shift in the transmission spectrum.

In reflection measurement, things are different. The reflectance can be calculated from the measured electric field of THz radiation as:

$$R(\nu) \equiv E_r(\nu)/E_o(\nu) = (\sqrt{\epsilon(\upsilon)} - 1)/(\sqrt{\epsilon(\upsilon)} + 1)$$

$$\sqrt{\epsilon(\upsilon)} = n(\nu) + j\alpha(\nu)c/2\pi\nu \approx n(\nu)$$

Preferably steps are taken to remove features in the detected radiation that relate to the system components. Therefore, preferably a reference measurement is taken in the absence of a sample. The signal detected in the absence of a sample can then be subtracted from the signal detected in the presence of a sample.

Alternatively the reference measurement can be taken in the presence of a reference sample with well known THz properties. Such a reference sample could be air, water or polyethylene.

Preferably, an absorption profile of the object can be determined by transforming the averaged time domain waveform into the frequency domain by means of a Fourier transform. The composition of the sample can be derived from this absorption profile.

Any absorption features will produce maxima and minima in the absorption profile. Conveniently, the derivative of the absorption profile with respect to frequency can be determined.

It is clear that the greater the area over which the sample is averaged the better the removal of the scattering features will be. However, averaging over the maximum area possible may not be necessary in order to resolve the true absorption features of a sample. Therefore, preferably, the method according to the first aspect of the present invention further comprises the step of progressively increasing the number of points that are irradiated until the scattering related effects are sufficiently reduced in order to determine the features of the object under investigation.

When an object is irradiated with an impulse of radiation then detected radiation will comprise an initial impulse feature and subsequently received signal. The signal that follows the initial impulse function is known as the "late time response". It has been suggested that this "late time response" provides useful information about the sample and therefore preferably the method according to the first aspect of the invention comprises the step of removing that portion of the averaged time domain waveform that corresponds to directly reflected/transmitted radiation and performing a Fourier transform on the remainder of the detected radiation in order to derive compositional information relating to the object.

In a second aspect of the present invention the "late time response" is analysed and there is therefore provided a method of investigating an object, comprising the steps of:

(a) irradiating the object with an optically-generated pulse of electromagnetic radiation, said pulse having a plurality of frequencies in the range from 100 GHz to 100 THz;

(b) detecting radiation transmitted and/or reflected from the object to obtain a time domain waveform;

(c) separating that portion of the detected radiation that corresponds to directly reflected or transmitted radiation and applying a Fourier transform to the remaining portion of the detected radiation.

In a third aspect of the present invention there is provided an apparatus for investigating an object comprising (a) a source of electromagnetic radiation for irradiating a point on the object with an optically-generated pulse of electromagnetic radiation, said pulse having a plurality of frequencies in the range from 100 GHz to 100 THz;

(b) a detector for detecting radiation transmitted and/or reflected from the object to obtain a time domain waveform;

(c) scanning means for sequentially irradiating a plurality of points on the object and (d) means for combining time domain waveforms from each of the plurality of points to produce a time domain waveform for the object which has been averaged over the plurality of points.

Compositional information relating to a sample can be determined by investigating the sample according to the method of the first aspect of the present invention. A compositional image of the sample can then be derived by imaging the sample through a spectral filter that is arranged only to let radiation relating to one (or more) of the components of the sample through to the detector. Therefore, in a fourth aspect of the present invention there is provided of imaging a sample comprising the steps of:

a) investigating the sample according to a method according to the first aspect of the invention;

b) deriving a spectral waveform from the time domain waveform obtained in step (a)

c) identifying the components of the sample from the spectral waveform in step (b)

d) re-irradiating the sample with an optically-generated pulse of electromagnetic radiation, said pulse having a plurality of frequencies in the range from 100 GHz to 100 THz e) detecting radiation transmitted and/or reflected from the object to obtain a time domain waveform, the detected radiation having first passed through at least one bandpass filter corresponding to at least one component of the sample f) generating an image from the radiation detected in step (e)

An alternative method of reducing the effects of scatter is to use a diffuse irradiating beam of radiation. Accordingly, in a fifth aspect of the present invention there is provided a method of investigating an object, comprising the steps of:

(a) irradiating the object with an optically-generated pulse of electromagnetic radiation, said pulse having a plurality of frequencies in the range from 100 GHz to 100 THz;

(b) detecting radiation transmitted and/or reflected from a first point on or within the object to obtain a time domain waveform;

wherein the irradiating pulse of radiation is focussed at a second point on or within the object.

The present invention will now be described with reference to the accompanying drawings in which:

FIG. 14b shows temporal waveforms associated with the image shown in FIG. 14a.

Figure 1:
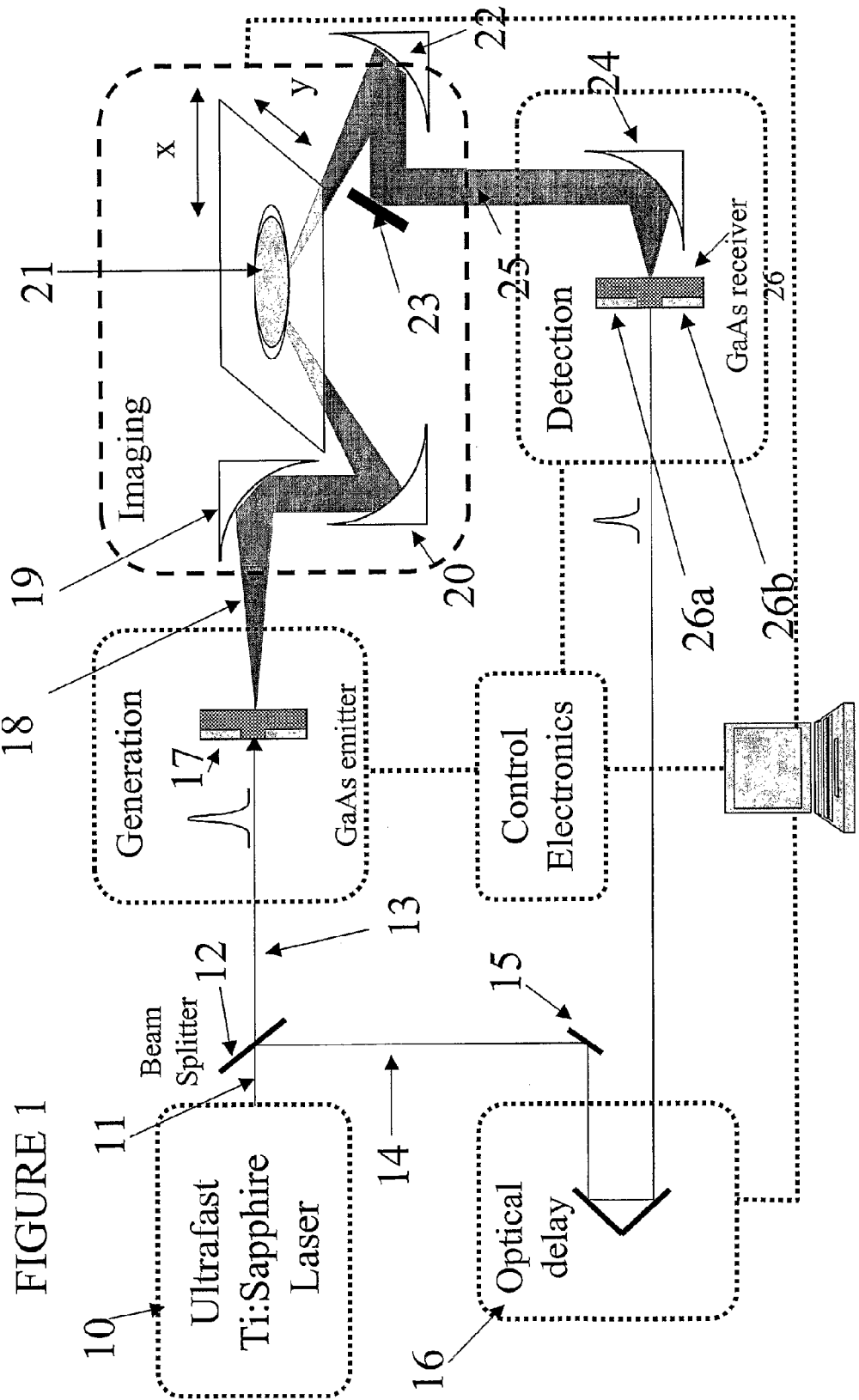
FIG. 1 illustrates a schematic of a pulsed terahertz reflection investigative technique utilised in a first embodiment of the present invention.

Referring to FIG. 1, a terahertz pulsed investigating arrangement is illustrated, which comprises an ultra-short pulse laser 10 which may be, for example, Ti:sapphire, Yb:Er doped fibre, Cr:LiSAF, Yb:silica, Nd:YLF, Nd:Glass, Nd:YAG, Alexandrite Yb:Phosphate Glass QX, Yb:GdCOB, Yb:YAG, Yb:KG d($WO_4$) or Yb:BOYS laser. This laser 10 emits pulses of radiation 11, such as a collimated beam of pulses, each of which comprise a plurality of frequencies. The pulses generated by the laser preferably having a pulse duration of less than 200 fs.

The beam of generated pulses is directed into beam splitter 12. The beam splitter splits the beam into a pump beam 13, which is used to irradiate the sample, and a probe beam 14, which is used during detection.

The probe beam 14 is directed, via plain mirror 15, into scanning delay line 16. Scanning delay line 16 is a variable optical delay, which in its simplest form comprises two mirrors that serve to reflect the beam through a 180° angle. Using a computer as a controller, these mirrors can be quickly swept backwards and forwards in order to vary the path length of the probe beam 14. In this way the scanning delay line 16 assists in matching the relative path lengths of the pump and probe beams. The probe beam is then focussed onto receiver 26 for combining with the Terahertz beam.

The pump beam 13 is directed onto a source 17. For pulsed approaches this source 17 preferably comprises a GaAs based photoconductive switch. GasAs based devices use the principle of photoconductive mixing to generate their THz output.

The THz radiation 18 emitted by the emitter 17 is directed via a hyper-hemispherical lens (not shown) towards a first parabolic mirror 19, which is preferably an off axis parabolic (OAP) mirror, as are all the parabolic mirrors referred to herein. The beam is then reflected off the first parabolic mirror 19 and onto second parabolic mirror 20, which directs the radiation onto sample 21.

To analyse a particular sample in situ, the sample 21 may be moved relative to the beam of radiation through the focal plane of the THz beam or the beam may be moved relative to the sample or both. As shown in FIG. 1, the sample may be placed on a translation stage to appropriately move the sample. This translation stage could move the sample one dimensionally along one axis of movement or through two or three axes of movement.

The THz radiation that is reflected from sample 21 is collected by third parabolic mirror 22 and onto a fourth parabolic mirror 24 via plain mirror 23. The fourth parabolic mirror 24 directs the reflected radiation 25 onto a second hyper-hemispherical lens (not shown) and onto a detector 26, such as an electro-optic detector or a photoconductive detector.

Photoconductive detectors comprise a detection member which may be, for example, GaAs, InGaAs, Si on Sapphire etc. The detection member 26 is used to detect both the amplitude and phase of the radiation emitted from the sample 20. In these detectors, the THz radiation 25 from the sample is incident on the back surface of the detection member 26. The radiation is collected by a lens (not shown), which may be hemispherical or have another shape. The Terahertz radiation 25 incident on the detection member 26 induces a photocurrent through the region between electrodes 26a and 26b, located on the opposing side of the detection member 26, which is being illuminated by the laser radiation. As the detector needs to know information about the phase of the radiation emitted from the generator 17, the radiation illuminating the region between electrodes 26a and 26b is preferably the probe beam 14, which carries this information. The current that can then be detected by the electrodes is proportional to the strength of the THz field 25.

The electrodes 26a, 26b may be of a simple diode formation embedded in a transmission line. Alternatively, they may be triangular and arranged in the shape of a bow-tie to form a so-called bow-tie antenna. They may also be interdigitated electrodes at the centre of a bow-tie or spiral antenna.

Figure 2:
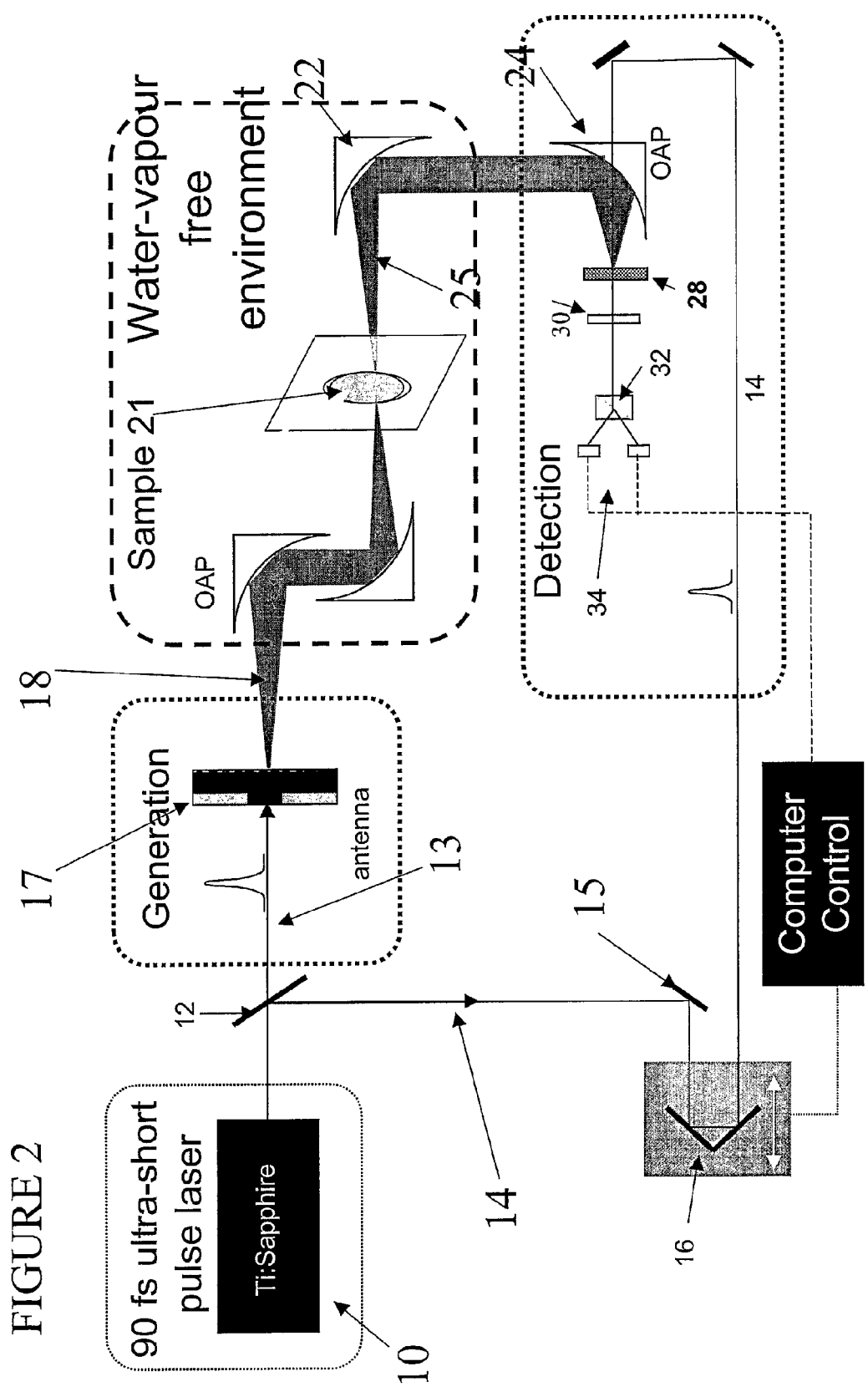
FIG. 2 illustrates a schematic of a pulsed terahertz transmission investigative technique utilised in a second embodiment of the present invention.

FIG. 2 illustrates an alternative pulsed arrangement, whereby the sample is investigated using transmitted radiation rather than reflected radiation and the detector is an EOS detector rather than a photoconductive detector. To avoid unnecessary repetition with respect to FIG. 1, like reference numerals will be used to denote like features.

In FIG. 2, it is apparent that a variable delay is introduced to the probe beam 14 and that the pump beam 13 is projected onto the sample in the same manner as was illustrated in FIG. 1. The sample in FIG. 2, however is now generally perpendicular to the incident pump beam, in order to maximise radiation transmission.

Transmitted radiation 25 is combined with the probe beam 14. One particularly popular way to do this is to use electro-optic sampling (EOS). In this technique, the transmitted THz beam 25 and the probe beam 14 co-linearly propagate through an EOS detector 28. The transmitted radiation 25 passes through the detector 28, which modulates the probe beam 14.

The EOS detector 28 may be comprised of any material which possesses good non-linear characteristics, such as GaAs or Si based semiconductors and $NH_4H_2PO_4$, ADP, $KH_2PO_4$, $KH_2ASO_4$, Quartz, $AlPO_4$, ZnO, CdS, GaP, $BaTiO_3$, $LiTaO_3$, $LiNbO_3$, Te, Se, ZnTe, ZnSe, $Ba_2NaNb_5O_{15}$, $AgAsS_3$, proustite, CdSe, $CdGeAs_2$, $AgGaSe_2$, $AgSbS_3$, ZnS, organic crystals such as DAST (4-N-methylstilbazolium).

The modulated beam is then passed into quarter wave plate 30. This serves to circularly polarise the emitted radiation. The circularly polarised light is then fed through a Wollaston prism 32, which divides the polarization of the light onto two orthogonal components. These two orthogonal components are then directed onto balanced photodiode assembly 34. The balanced photodiode assembly comprises two photo diodes to respectively detect each of the orthogonal components from the Wollaston prism 32. The output of the photodiodes are then linked together such that the balanced photodiode assembly 34 only outputs an electrical signal if there is a difference between the readings of the two photodiodes. This output signal corresponds to the strength of the transmitted THz beam 25.

This is because, where there is no THz beam present, there is no difference between the two photodiode signals. However, where there is a THz beam 25, the THz beam 25 serves to make the radiation exiting the detector 28 slightly elliptically polarised. This change in the polarization still remains after the radiation is passed through quarter waveplate 30. Extracting the orthogonal components of this radiation using prism 32 causes a different signal to be measured at the two photodiodes, and hence balanced photodiode assembly 34 outputs a signal corresponding to the strength of the THz field.

Therefore EOS detection enables the phase and amplitude of the transmitted radiation to be detected. It is to be appreciated that it will be apparent to those skilled in the art that this type of analysis could be performed for any type of detector.

It is also to be appreciated that it is also possible to combine the arrangements of FIGS. 1 and 2, whereby both reflected and transmitted radiation from the sample is measured.

Further, rather than combining the beam which has been reflected from or transmitted by the sample with the probe beam 14, it is also possible to combine the THz beam with another beam of radiation which has substantially the same wavelength or which differs in frequency by at most 10 GHz. Such combined radiation can be detected using a bolometer, Schottky diode etc.

Figure 3:
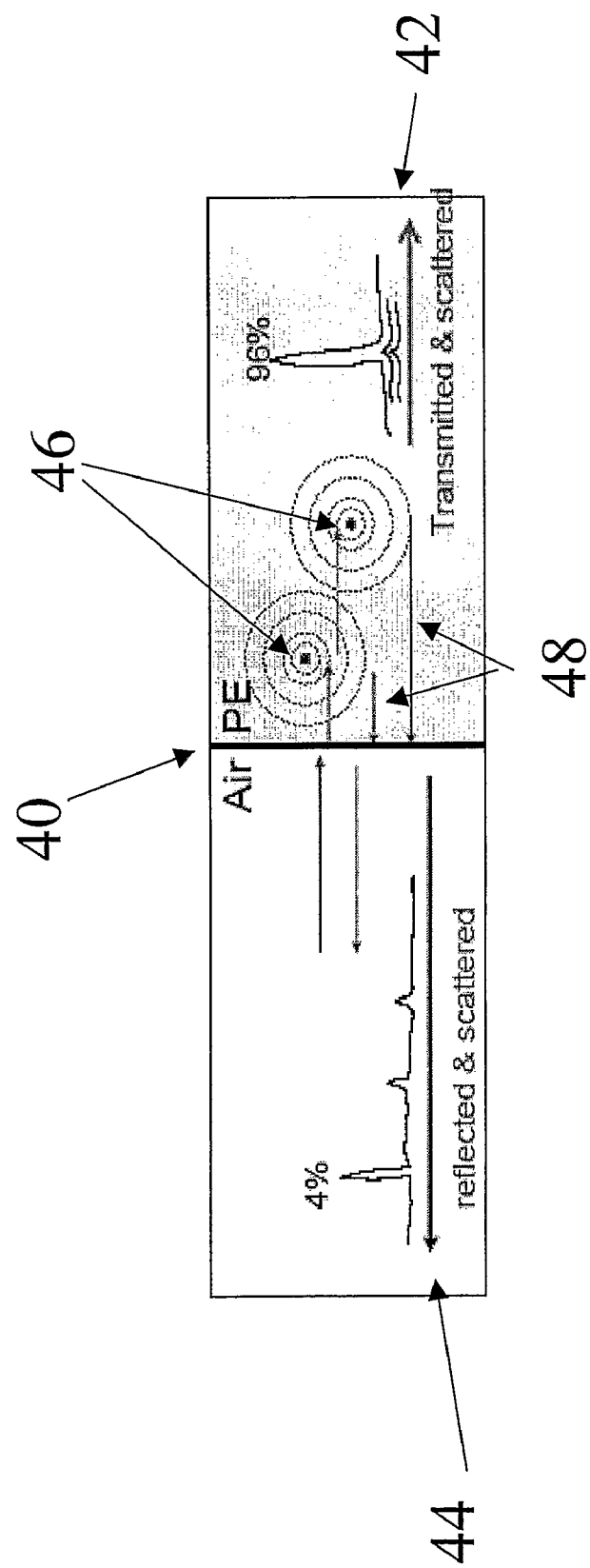
FIG. 3 shows a schematic representation of an air/polythene interface showing the various reflection, transmission and scattering components

FIG. 3 shows a schematic representation of an air/polythene interface 40 showing the various reflection, transmission and scattering components. It can be seen that the transmitted signal 42 is much stronger than the reflected signal 44—96% to 4%.

Scattering centres 46 introduce additional scattered signals 48. The reflected beam is much more susceptible to these scattered pulses as it has a weaker intensity. In both transmission and reflection however scattering events can give rise to false spectral features.

Figure 4:
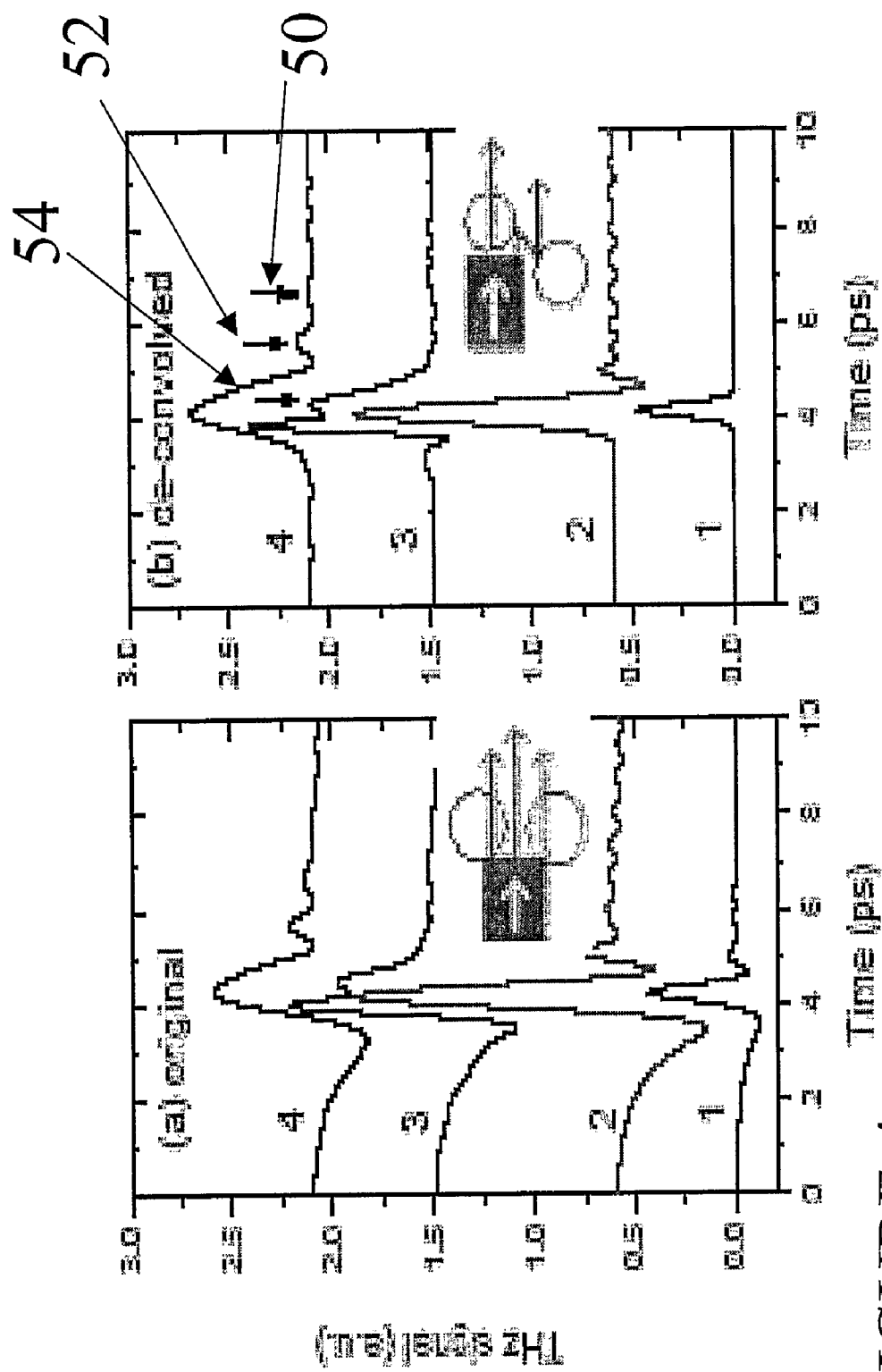
FIGS. 4a and 4b show time domain waveforms for samples composed of sucrose and PE powder.

FIG. 4a shows four time domain waveforms for samples composed of 60 mg of sucrose and 260 mg of PE powder. Each sample was measured within a powder cell. Curve 1 shows the recorded waveform when shows a reference trace of an empty powder cell. Curve 2 shows a sucrose sample with particle sizes of 53-75 µm. Curve 3 shows a sucrose sample with particle sizes greater than 250 µm. Curve 4 is also for particles greater than 250 µm but at a different location in the powder cell.

In order to show the waveforms due to the sample only, the recorded waveforms from FIG. 4a were then de-convolved with the reference trace (curve 1). The de-convolved THz waveforms are shown in FIG. 4b. It should be noted that in both FIGS. 4a and 4b the curves have been offset for clarity. Also, the signal intensity of curve 1 has been reduced by a factor of 4.

The presence of features due to scattering can clearly be seen in FIG. 4b (arrows 50, 52 and 54) and are more common with increasing size of the sucrose particles. These scattering features would give rise to false spectral features if the data of FIG. 4b were analysed in the frequency domain (by Fourier transforming the data).

Figure 5:
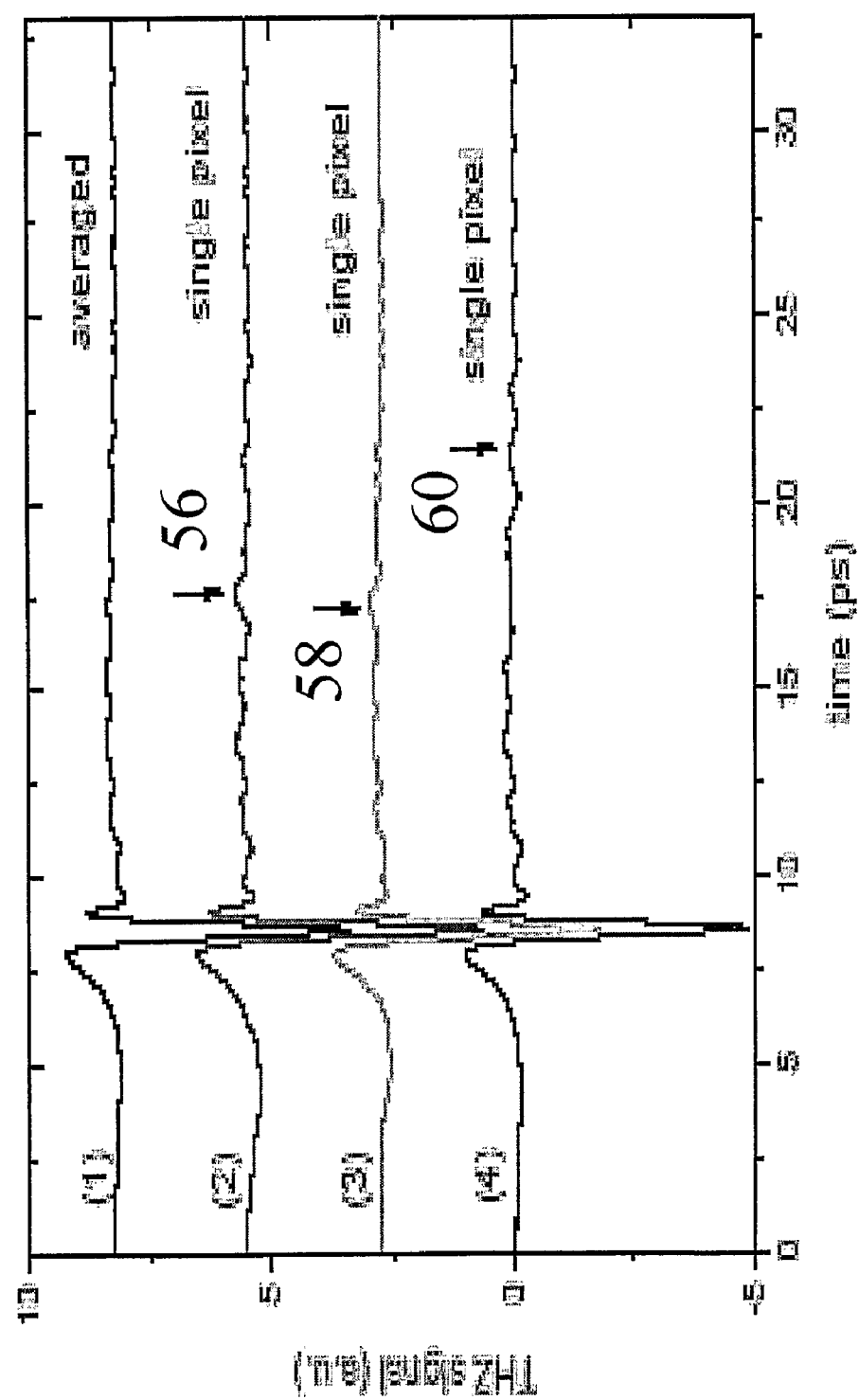
FIG. 5 shows a series of waveform traces measured from a mixture of fine lactose particles and large sucrose particles (500-800 μm size/diameter).

FIG. 5 shows a series of waveform traces measured from a mixture of fine lactose particles and large sucrose particles (800 µm size/diameter). Curves 2, 3 and 4 show readings taken from three different points on the sample. It can be seen that after the main initial pulse there is a series of ripples caused by the absorption/reflection characteristics of the sample. Three additional features (highlighted by arrow 56 in curve 2, arrow 58 in curve 3 and arrow 60 in curve 4) are however visible in these curves. These additional features come from scattering events and will result in false spectral features following a Fourier transform of the data.

Curve 1 shows an averaged waveform (including the three curves 2, 3 and 4) taken over an area of 5 mm². It can be seen that the scattering related features are now absent from the waveform.

Figures 6A, 6B, 7A, 7B, 8A, 8B:
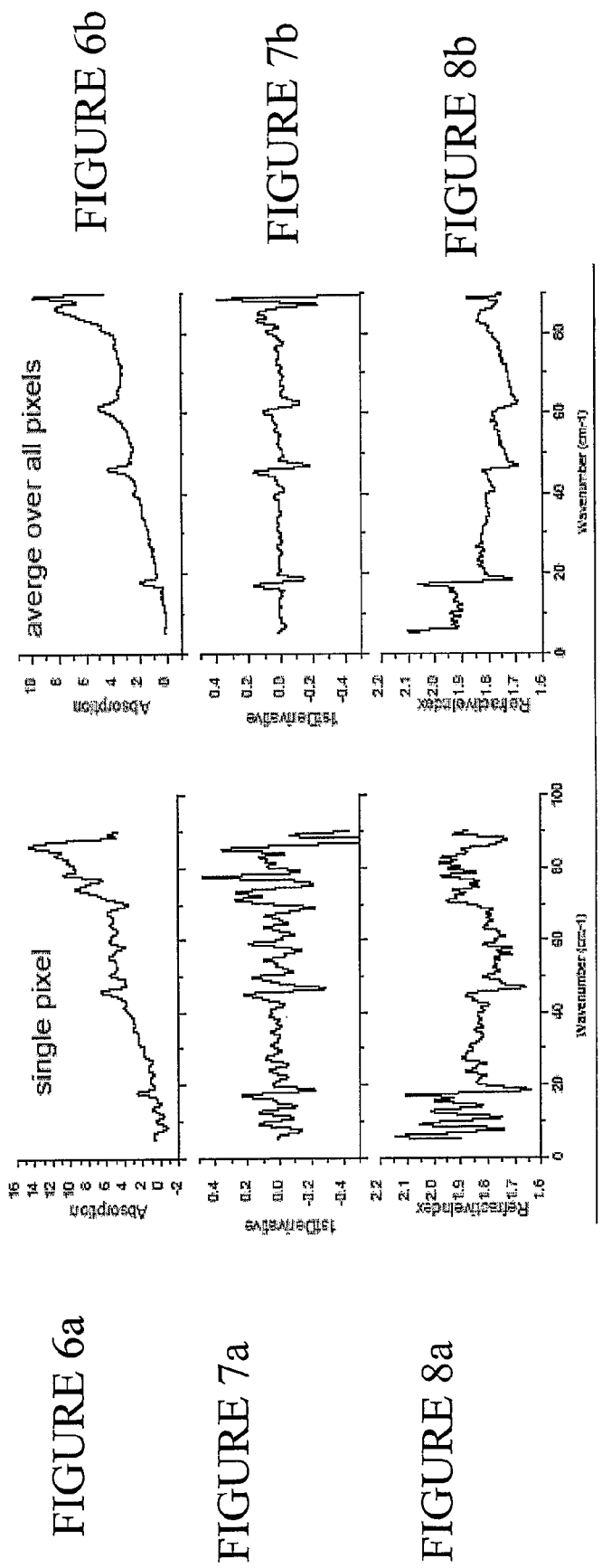
FIGS. 6a and 6b show absorption plots at a single point (FIG. 6a) and an averaged dataset (FIG. 6b).
FIGS. 7a and 7b show the first derivative of the absorption plots of FIGS. 6a and 6b.
FIGS. 8a and 8b show refractive index plots of the sample imaged in FIGS. 6a and 6b.

FIGS. 6a and 6b show a comparison in the frequency domain between a spectroscopic measurement at a single point (FIG. 6a) and an averaged dataset (FIG. 6b). In FIG. 6a a Fourier transform of a waveform trace (similar to those in Curves 2-4 of FIG. 5) has been plotted. This therefore corresponds to an absorption profile.

In FIG. 6b the waveform data has been averaged first and the Fourier transform of the averaged data has been plotted. It can been seen that, in comparison to FIG. 6b, the trace in FIG. 6a comprises a number of false spectral features.

The trace in FIG. 6b shows a rising level of absorption with increasing wavenumber. This is due to absorption by the sample and/or the scattering of polyethylene (PE). The phase difference between reference and sample measurement will also cause a similar shift of the absorption spectrum. In order to remove this aspect and aid interpretation of the spectral features the so-called "First derivative" (d(absorption)/a(Frequency) has been plotted in FIGS. 7a and 7b. It should be noted that FIG. 7a corresponds to FIG. 6a and FIG. 7b to 6b.

It is clear from FIGS. 7a and 7b that the presence of spectral features in FIG. 7a makes spectral analysis virtually impossible.

FIGS. 8a and 8b show plots of refractive index versus wavenumber. The refractive index is calculated from time domain and phase information. Again, FIG. 8a corresponds to FIGS. 6a and 7a. FIG. 8b corresponds to FIGS. 6b and 7b. It can be seen that compared to FIG. 8b the presence of scattering events in FIG. 8a introduces many errors into the derivation of the refractive index.

Figure 9:
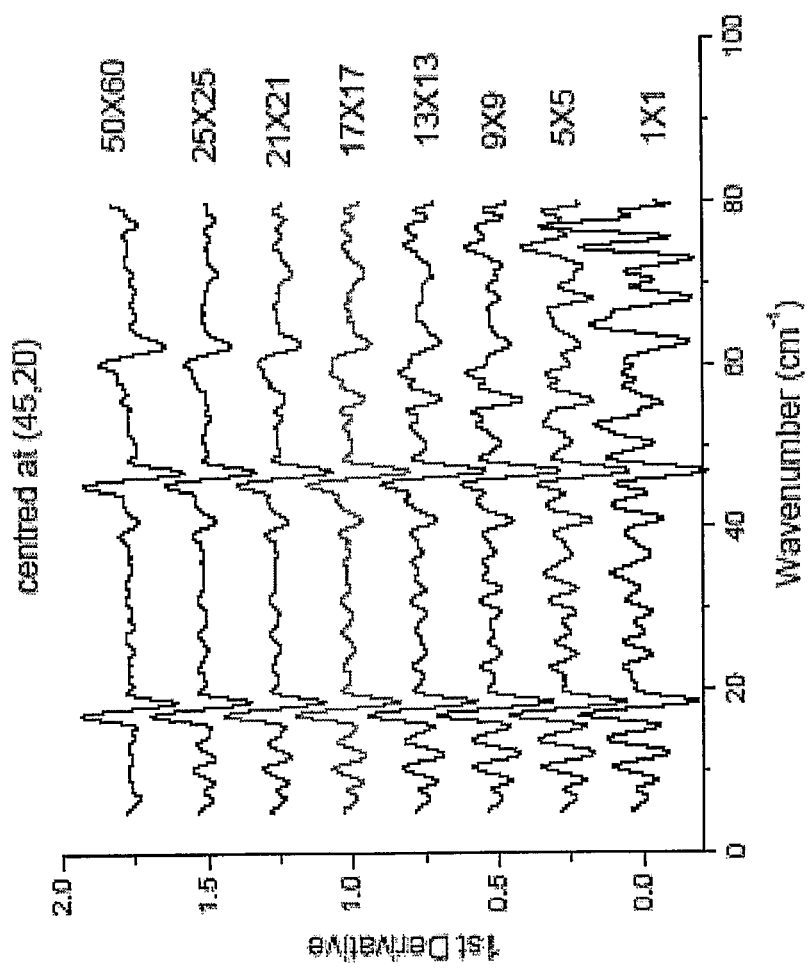
FIG. 9 shows various THz reflection spectra of the same sample for various sample areas.

FIG. 9 shows various THz reflection spectra of the same sample obtained by averaging over a sample area of different size. The sample comprised a mixture of sucrose and lactose particles.

The number of points (pixels) used in averaging is shown next to each spectrum and the images have been off-set for clarity. It is clear that averaging over a larger sample area improves the results. However, in this example it can be seen that a sample area of 13×13 pixels is sufficient to resolve the absorption features of lactose and sucrose.

A sample that is investigated using reflection spectroscopy will return a temporal waveform that comprises an initial impulse feature corresponding to the reflection from the surface of the sample and subsequent waveform data. By analysing the waveform trace following the initial impulse feature further information can be derived about a sample. This type of analysis is often referred to as the "late time response" of a sample.

Figure 10:
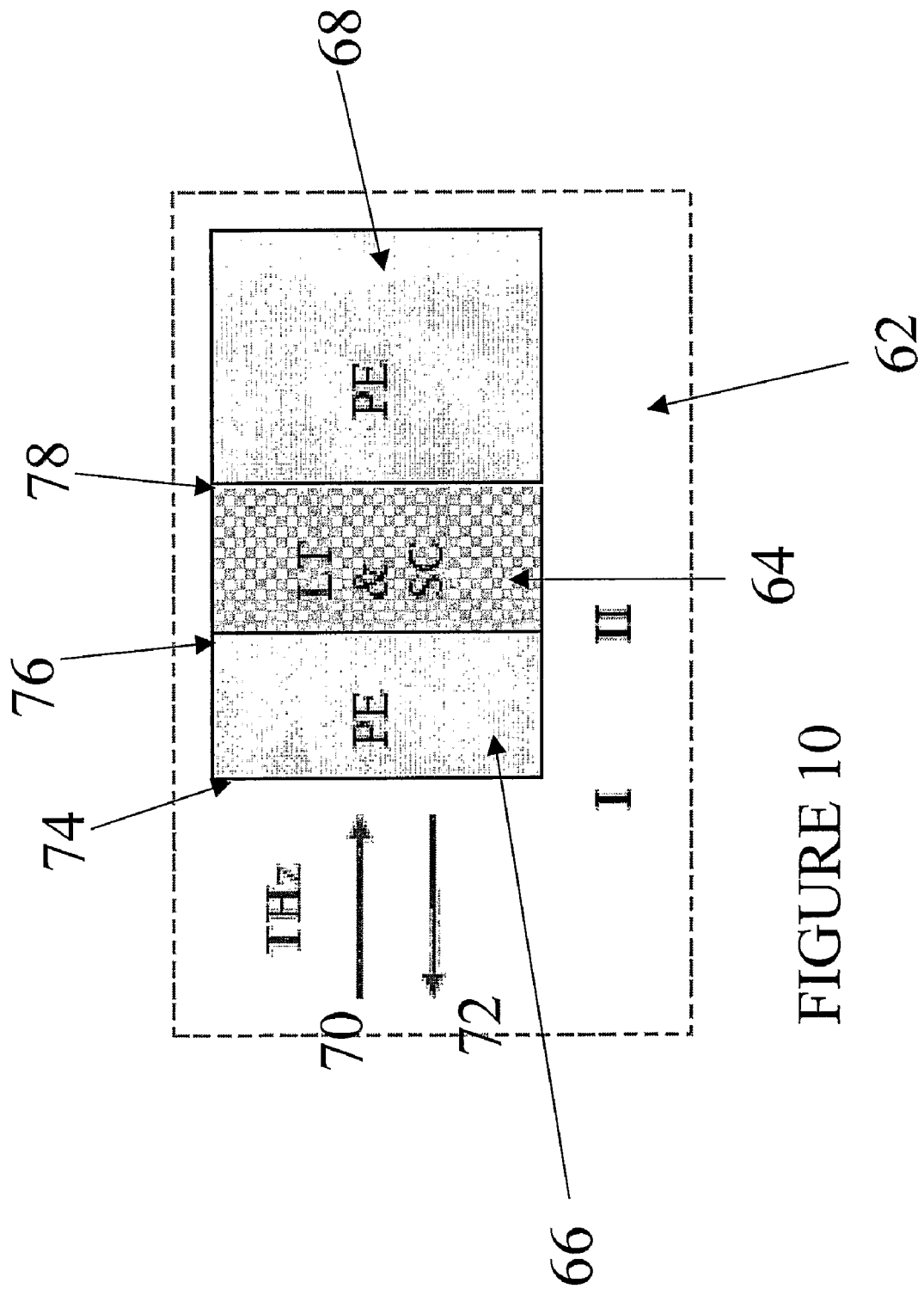
FIG. 10 shows a schematic of a layered PE/lactose/PE sample.

FIG. 10 shows a layered sample 62. A central layer 64 of a lactose and sucrose mixture is sandwiched between two layers of polythene 66, 68. Terahertz radiation 70 is incident on one of the polythene layers and the reflected radiation 72 detected. The sample comprises an air/PE interface 74 and two PE/LT interfaces 76, 78.

Figure 11:
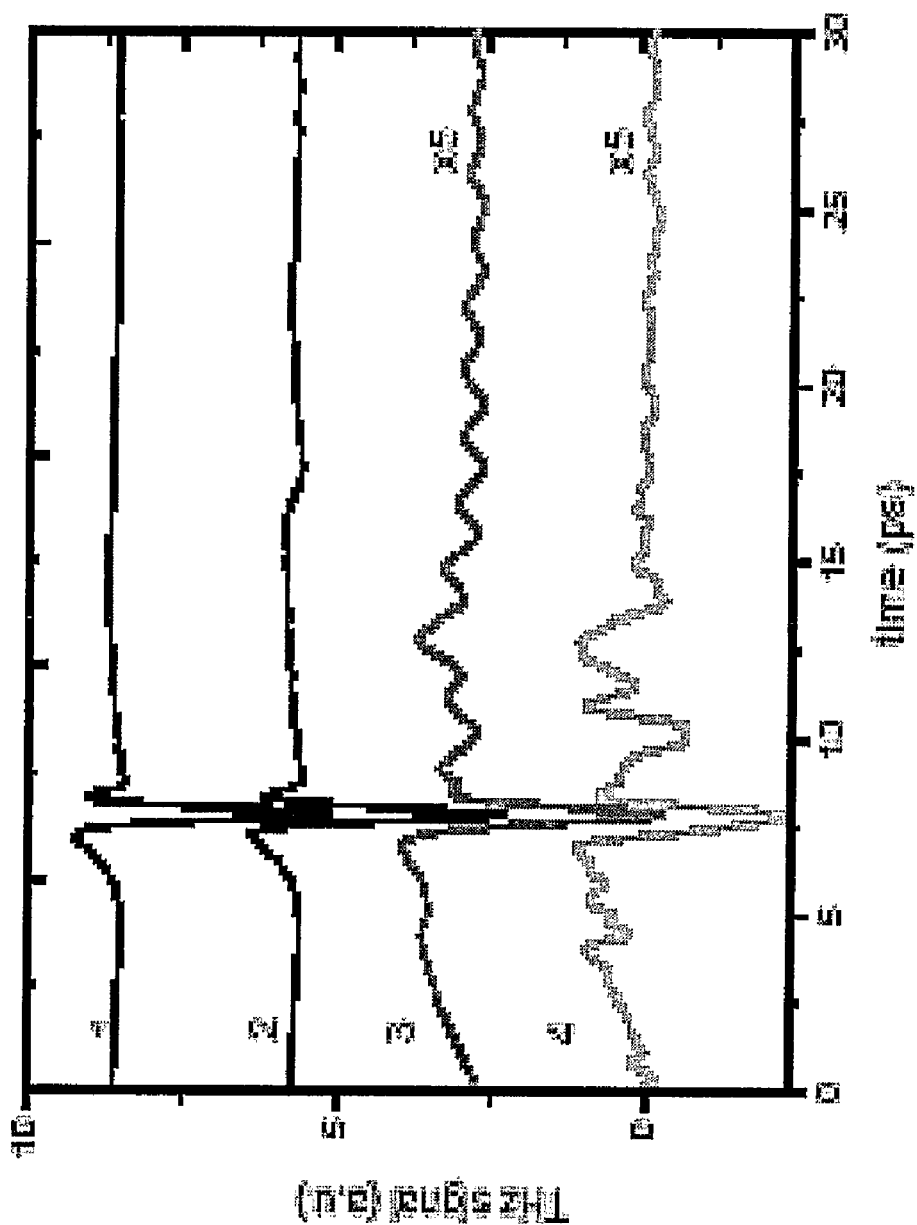
FIG. 11 shows various temporal waveform traces obtained from the sample shown in FIG. 10

FIG. 11 shows temporal waveform traces obtained from the sample shown in FIG. 10. Curve 1 is a polythene reference trace obtained by focussing the incident radiation on a separate reference sample. Curve 2 shows the trace obtained by focussing incident radiation on the air/PE interface. Curves 3 and 4 show the trace obtained by focussing the incident radiation at the first PE/LT interface (Curve 4 is obtained at a single pixel whilst curve 3 is averaged over the whole area). The THz signal reflected from the first PE/LT interface is much weaker than that from air/PE, '×5' means that the corresponding signal is multiplied by a factor of 5.

Figure 12:
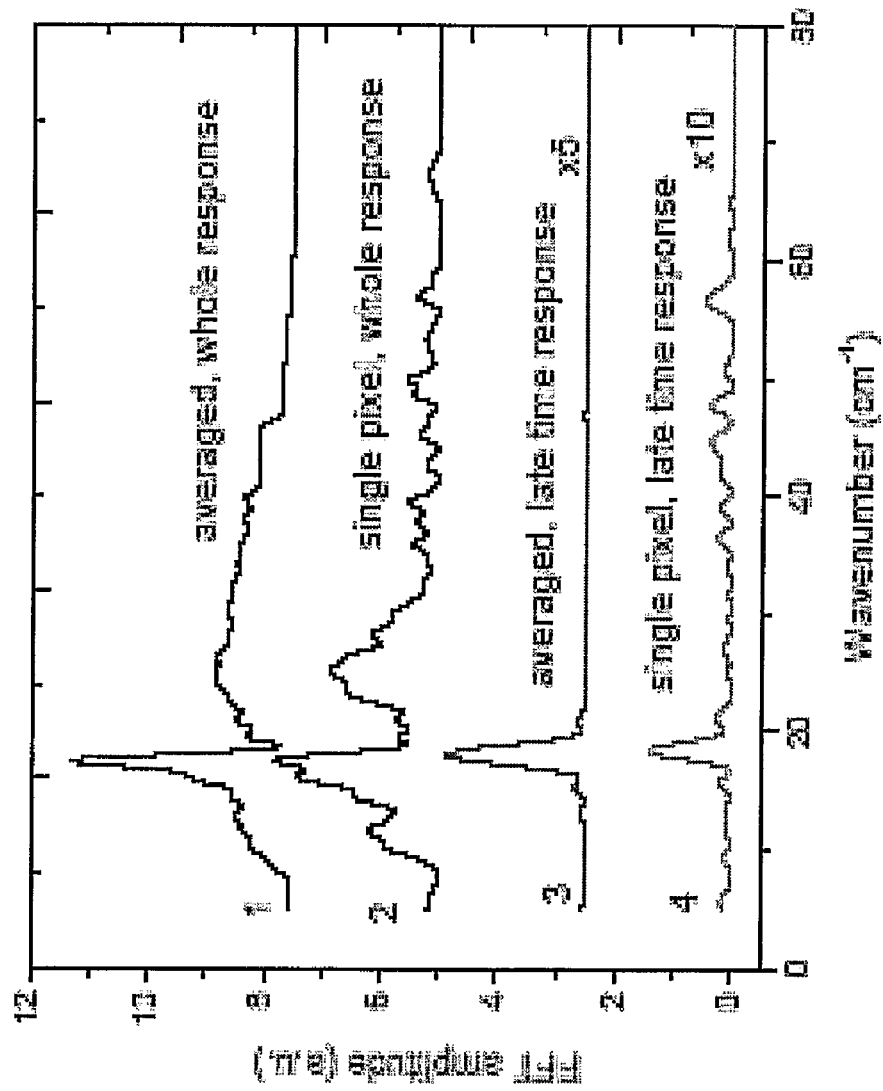
FIG. 12 shows various spectral plots obtained from the sample shown in FIG. 10.

FIG. 12 shows a comparison of the whole response from the sample of FIG. 10 with the late time response measured from the sample following a Fast Fourier Transforms. In each case the incident radiation was focussed on the LT/PE interface.

Curves 1 and 2 relate to the whole response. Curve 1 represents the averaged response from the sample and curve 2 shows a typical response from one imaging point. Curves 3 and 4 show the late time response from the sample. It is clear that the spectral feature of lactose at 18 cm$^{-1}$ can now be clearly resolved. Curve 3 represents a combination of late time response and averaging.

Figure 13B:
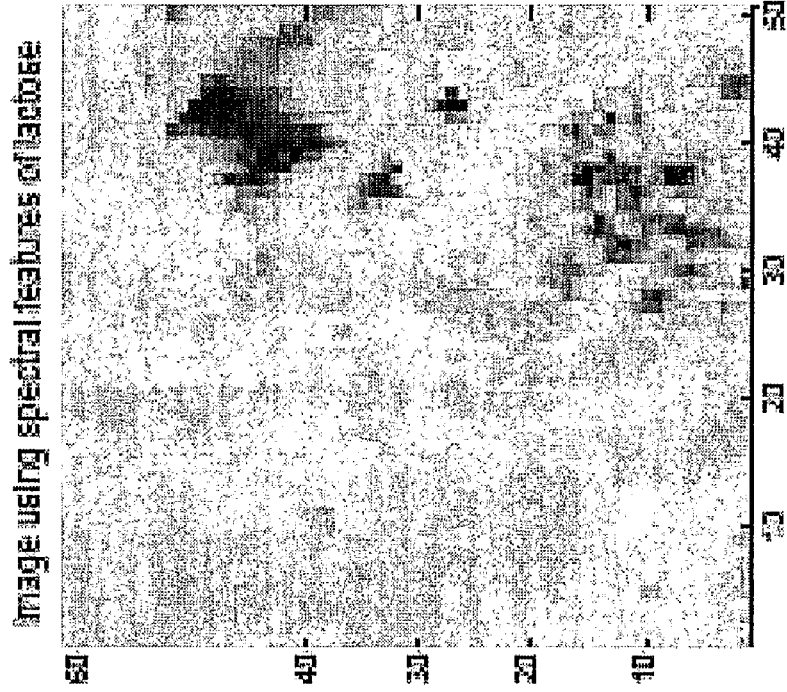
FIG. 13 shows a chemical mapping image of a sucrose/lactose/polyethylene sample
Figure 13A:
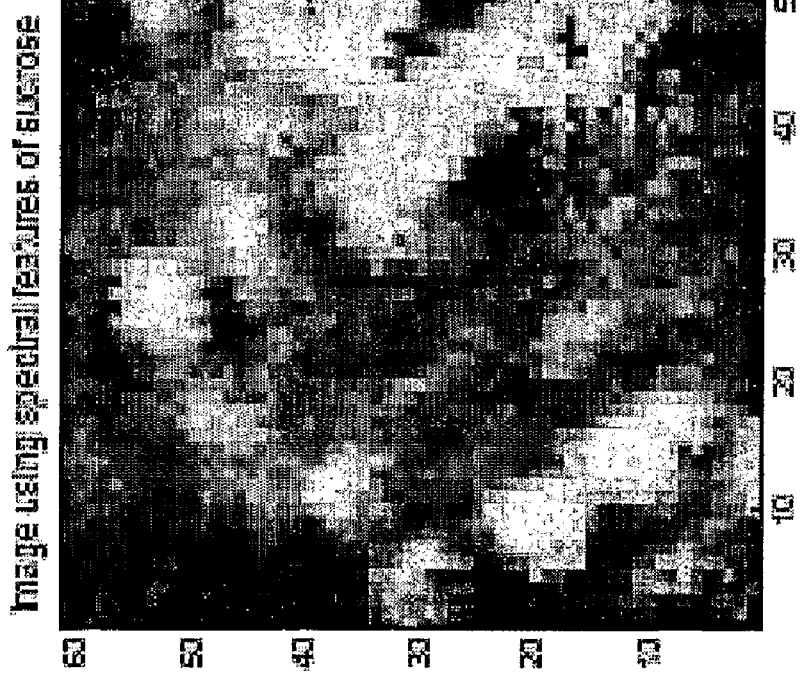

By using a method relating to the present invention it is possible to identify the true spectral components of a sample. Once these features have been identified it is possible to image the sample at the wavelengths relating to the components of the sample. In this way a spectral image can be compiled of the sample. FIG. 13 shows a chemical mapping image of a sucrose/lactose/polyethylene sample using the spectral features of (a) sucrose and (b) lactose.

Figure 14B:
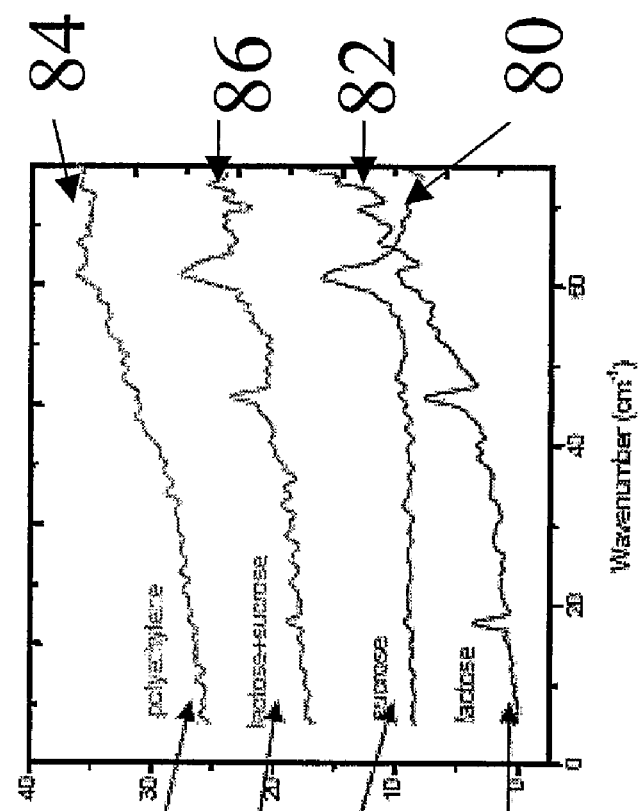
Figure 14A:
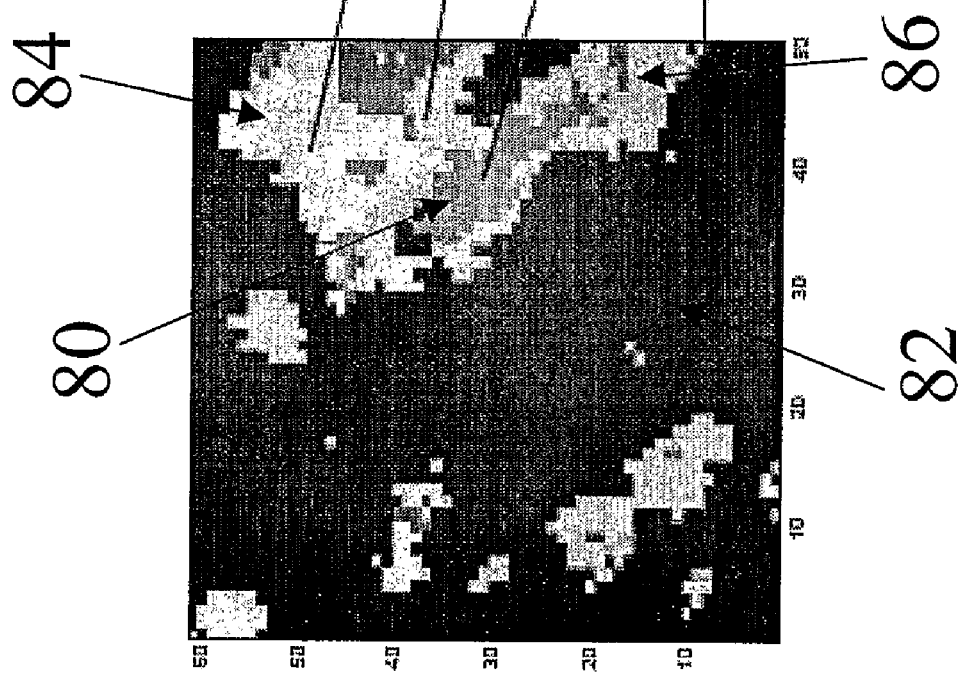
FIG. 14a shows a further chemical distribution image of the surface of a sample.

FIG. 14a shows a further chemical distribution image of the surface of a sample. The spectral features of sucrose, lactose and polyethylene have been used to identify the location of the components on the surface of the sample. Sucrose is denoted by 80, lactose by 82, and polyethylene by 84. The area labelled 86 comprises both lactose and sucrose. The corresponding THz reflection spectra are shown in FIG. 14b.

Figure 15:
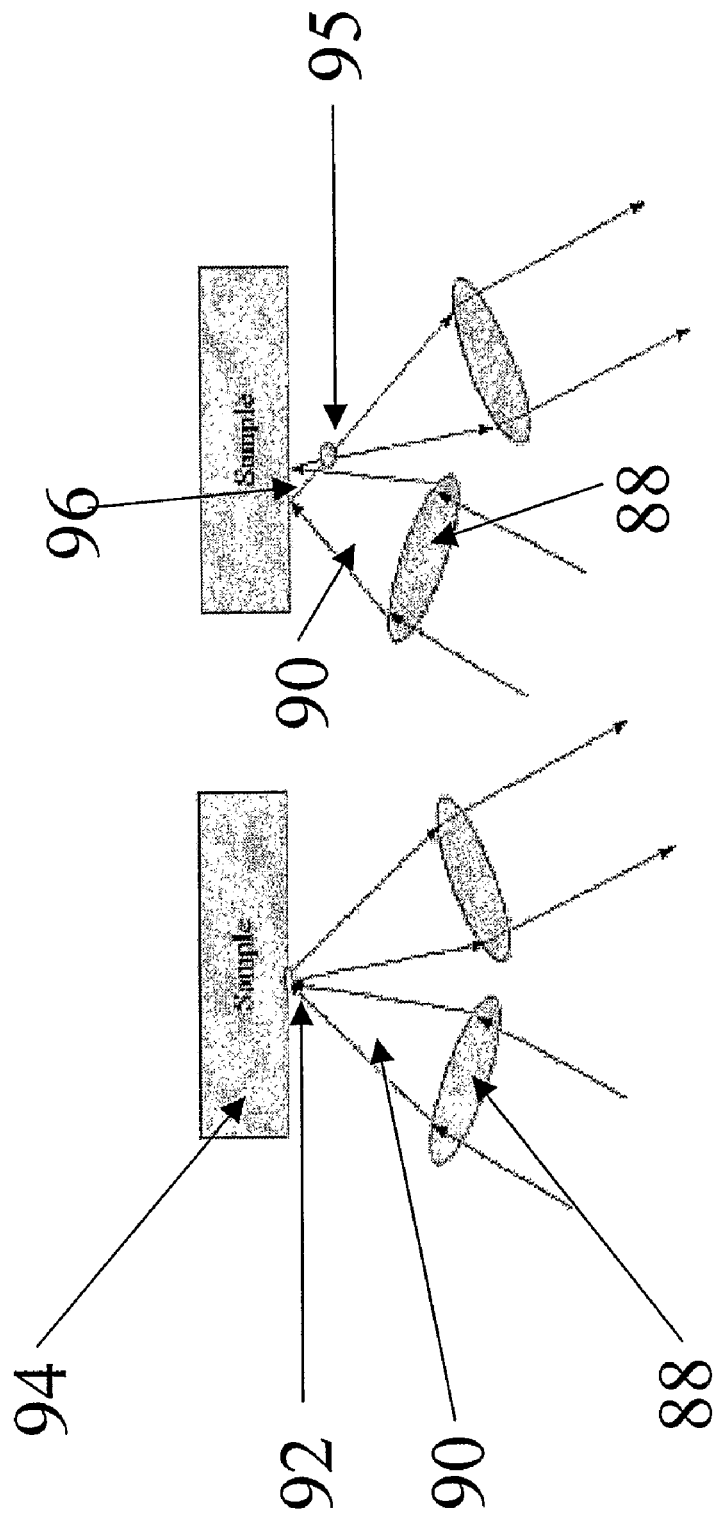
FIG. 15 shows an imaging configuration for a THz system

An alternative method of reducing the effects of scatter is to use a diffuse irradiating beam of radiation. Such an arrangement is shown in FIG. 15. In a typical system configuration the emitter optics 88 are arranged to focus the irradiating THz radiation 90 on a single point 92 on the sample 94. However, as an alternative the focus 95 could deliberately be moved such that a "diffuse" THz irradiating beam 96 probes the sample. This will have a similar effect to the "averaging" method of the first aspect of the invention and consequently scattering effects will tend to cancel each other out across the width of the beam.

The invention claimed is:

1. A method of investigating an object, comprising the steps of:
   (a) irradiating the object with an optically-generated pulse of electromagnetic radiation, said pulse having a plurality of frequencies in the range from 100 GHz to 100 THz;
   (b) detecting radiation transmitted and/or reflected from the object to obtain a time domain waveform;
   (c) repeating steps (a) and (b) for a plurality of points on the object;
   (d) combining data from step (c) to produce a time domain waveform for the object which has been averaged over the plurality of points; and
   (e) removing the directly reflected or directly transmitted portion of the signal obtained in step (d) and applying a Fourier transform to the remaining portion of the waveform.

2. A method of investigating an object, comprising the steps of:
   (a) irradiating the object with an optically-generated pulse of electromagnetic radiation, said pulse having a plurality of frequencies in the range from 100 GHz to 100 THz;
   (b) detecting radiation transmitted and/or reflected from the object to obtain a time domain waveform;
   (c) separating that portion of the detected radiation that corresponds to directly reflected or transmitted radiation and applying a Fourier transform to the remaining portion of the detected radiation.

3. A method of investigating an object, comprising the steps of:
   (a) irradiating the object with an optically-generated pulse of electromagnetic radiation, said pulse having a plurality of frequencies in the range from 100 GHz to 100 THz;
   (b) detecting radiation transmitted and/or reflected from a first point on or within the object to obtain a time domain waveform;
   wherein the irradiating pulse of radiation is focused at a second point on or within the object.

* * * * *